United States Patent [19]
Dumont et al.

[11] Patent Number: 5,116,756
[45] Date of Patent: May 26, 1992

[54] PROCESS FOR PRODUCING FK-506

[75] Inventors: Francis Dumont, Rahway; George M. Garrity, Westfield, both of N.J.; Isabel M. Fernandez; Teresa D. Matas, both of Madrid, Spain

[73] Assignee: Merck & Co., Inc., Rahway, N.J.

[21] Appl. No.: 646,555

[22] Filed: Jan. 28, 1991

[51] Int. Cl.$^5$ .................. C12R 1/465; C12P 17/16
[52] U.S. Cl. .................. 435/253.5; 435/118; 435/886
[58] Field of Search .................. 435/253.5, 118, 886

[56] References Cited

U.S. PATENT DOCUMENTS 3,244,592 4/1966 Arai .
4,894,366 1/1990 Okuhara et al. .................. 435/118

FOREIGN PATENT DOCUMENTS 0184162 6/1986 European Pat. Off. .

OTHER PUBLICATIONS

J. Antibiotics A15: 231-232 (1962).

Primary Examiner—Herbert J. Lilling
Attorney, Agent, or Firm—Robert J. North; Charles M. Caruso

[57] ABSTRACT

Described is a new process for producing the macrolide immunosuppressant, FK-506 under fermentation conditions utilizing the microorganism, Streptomyces sp., (Merck Culture Collection No. MA 6858) ATCC No. 55098. The immunosuppressant is useful in preventing human host rejection of foreign organ transplants, e.g. bone marrow and heart transplants.

1 Claim, No Drawings

PROCESS FOR PRODUCING FK-506

BACKGROUND OF THE INVENTION

1. Field of the Invention

This invention relates to a new process for producing the immunosuppressant agent, FK-506, utilizing the microorganism Streptomyces sp., (MA 6858) ATCC No. 55098.

2. Brief Description of Disclosures in the Art

In 1983, the U.S. FDA licensed cyclosporin, an extremely effective anti-rejection drug that revolutionized the field of organ transplant surgery. The drug acts by inhibiting the body's immune system from mobilizing its vast arsenal of natural protecting agents to reject the transplant's foreign protein.

As effective as that drug is in fighting transplantation rejection, it suffers drawbacks in causing kidney failure, liver damage and ulcers which in many cases can be very severe.

U.S. Pat. No. 4,894,366 and EPO Publication No. 0184162 to Fujisawa, hereby incorporated by reference, describe a new macrolide immunosuppressant, FK-506, which is reputed to be 100 times more effective than cyclosporin. The macrolide is produced by fermentation of Streptomyces tsukubaensis, a monotypic species of Streptomyces.

Processes or microoganisms for the production of these immunosuppressive agents, particularly FK-506, which may lack the side effects of cyclosporin, are constantly being searched for in the field.

SUMMARY OF THE INVENTION

It has been found that the immunosuppressant, FK-506 (FR-900506), can be obtained by the fermentation of the microorganism Streptomyces sp., ATCC No. 55098, under submerged aerobic conditions in an aqueous carbohydrate medium, containing a nitrogen nutrient, said conditions being conducted at a pH of about 7. The produced compound possesses and displays all of the physical and chemical characteristics of FK-506 (FR-900506) as described in EPO Publication No. 0184162.

In accordance with this invention, there is provided a process for producing the immunosuppressant, identified as FK-506, comprising the step of culturing a strain of Streptomyces sp., (MA 6858) ATCC No. 55098, or mutant thereof, produced by conventional methods, under submerged aerobic fermentation conditions in an aqueous carbohydrate medium, containing a nitrogen nutrient, for a sufficient time to produce the product FK-506.

Also provided is the novel microorganism, Streptomyces sp., (MA 6858) ATCC No. 55098 in biologically pure form.

DETAILED DESCRIPTION OF THE INVENTION AND PREFERRED EMBODIMENTS

The present invention involves the fermentation of Streptomyces sp., (MA 6858) ATCC No. 55098 to produce FK-506 which has the following structure:

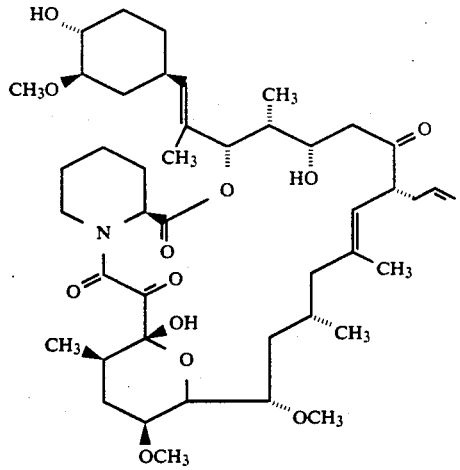

The microorganism is currently on restricted deposit with the American Type Culture Collection, 12301 Parklawn Drive in Rockville, Md. as under the Budapest Treaty ATCC No. 55098. The biological characteristics are briefly described hereinbelow.

Based upon these data, the microorganism is identified as member of the genus Streptomyces.

The following is a general description of Streptomyces sp. strain MA 6858, ATCC No. 55098.

MA 6858

Observations of growth, general cultural characteristics and carbon source utilization were made in accordance with the methods of Shirling and Gottlieb (Internat. J. System, Bacteriol. 16:313–340). Chemical composition of the cells was determined using the methods of Lechevalier and Lechevalier (in Actinomycete Taxonomy, A. Kietz and D. W. Thayer, Ed. Society for Industrial Microbiology, 1980). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985). DNA-DNA homology of the strains was determined by the method described by Kurtzman, et al (Int. J. Syst. Bacteriol. 30:208–216)

Source—MA 6858

This culture was isolated from the dung of white tailed deer, Poverty Creek Drainage, Montgomery County, Virginia.

Analysis of Cell Wall Composition—MA 6858

Peptidoglycan contains L-diaminopimelic acid. Whole cell carbohydrate analysis reveals glucose.

General Growth Characteristics

Good growth on yeast malt extract agar (YME), inorganic salt starch agar, peptone iron agar and oatmeal agar. Fair growth on glycerol asparagine agar, Czapek's agar, trypticase soy agar and tap water agar supplemented with NZ-amine (Sheffield Chemical Co.) Sparse growth on tap water agar. Culture also grows in tryptone yeast extract broth. Culture grows at 27 C., but not at 37 C.

Colony Morphology (on YME at 21 d)

Substrate mycelium is medium yellow brown. Aerial mycelium white. Spore mass, when present, is yellowish-white to light gray. Colonies are opaque, raised, with entire to lobate edges, rough textured and rubbery in consistency.

Micromorphology

Aerial mycelia (0.72 μm) arise in tufts from a substrate mycelium and are branched and flexous. Sclerotia are observed in the aerial mass when the culture is grown on either YME or oatmeal agar. In mature cultures, the aerial mycelium may terminate in flexous chains of spores at 7–28 d. Sporulation occurs in YME, inorganic salts-starch agar. Chains of spores are contained in a fibrous sheath and may be terminated by a "knot-like" structure at the apex. This characteristic is most notable on Czapek's agar and may appear as sporangia-like vesicles on immature cultures.

Miscellaneous Physiological Reactions

Culture produces $H_2S$ in peptone-iron agar but does not produce melanoid pigments. Carbon source utilization pattern is as follows: good utilization of β-D-lactose, D-mannose; moderate utilization of cellobiose, D-fructose, α-D-lactose; poor utilization of L-arabinose, D-mannitol, D-raffinose, L-rhamnose; no utilization of D-arabinose, inositol, D-maltose, sucrose, D-xylose, L-xylose.

DNA-DNA Homology

DNA-DNA homology studies were carried out with the three Streptomyces strains known to produce this class of compounds. (MA 6492 *Streptomyces tsukubaensis*, FK-506 patent strain (See EPO 0 184 162); MA 6531 *Streptomyces hygroscopicus* subsp. *yakushimaensis*, FK-520/FK-523 patent strain (See EPO 0 184 162); MA 6475 *Streptomyces hygroscopicus* subsp. *ascomyceticus*, FK-520 producing strain (See U.S. Pat. No. 3,244,592). These experiments reveal that MA 6858 exhibits intermediate levels of homology with these three strains (MA 6492—54%, MA 6531—52%, MA 6475—48% at Tm-25C). In addition, reassociation kinetics show that the genome of MA 6858 is comparable in size to MA 6531 and MA 6475 but approximate 30% larger than that of MA 6492.

Diagnosis

Cell wall analysis reveals that MA 6858 has a type I cell wall and morphological studies reveal that the culture produces spores on straight to flexous sporophores which arise from the aerial mycelium. These are characteristics typical for strains of Streptomyces. A comparison of the phenotypic data of MA 6858 with that of the validly published species of Streptomyces in the literature shows that the strain has some similarity to *Streptomyces setonii* and *Streptomyces gougeroti*, but neither of those strains are reported to produce sclerotia, pseudoosporangia or other morphological structures on the aerial mycelia. In addition, both of those cultures are reported to utilize D-glucose whereas MA 6858 does so only sparingly. The following tables list the cultural characteristics and carbohydrate utilization pattern of MA 6858.

| Cultural characteristics of *Streptomyces sp.* MA6858 at 21 days | | | | |
|---|---|---|---|---|
| Medium | Amount of Growth | Aerial Mycelium and/or Spores | Soluble Pigments | Reverse Color |
| Yeast Extract Malt Extract | good | Aerial mycelium yellowish white (92 yWhite). Spores borne in straight chains. Sclerotia observed in aerial growth. | none noted | Medium yellow brown (76 m.yBr) |
| Glucose Asparagine | fair | Aerial mycelium sparse, white (263 White). No sporulation evident. | none noted | light yellow brown (73 l.yBr) |
| Inorganic Salts Starch | good | Aerial mycelium yellowish white (92 yWhite). Spores borne in long chains. Sclerotia also found. Starch vigorously hydrolyzed. | none noted | Pale orange yellow (73 p.OY) |
| Oatmeal | good | Aerial mycelium pale orange yellow (73 pOY). Spores borne in straight chains. Sclerotia present in aerial mass. | none noted | Light orange yellow (70 l.OY) |
| Tap Water | sparse | No aerial growth observed. | none noted | |
| Czapek | fair | No aerial growth observed. | none noted | |
| Peptone Iron | good | | Melanin negative, $H_2S$ positive. | |

| Carbohydrate utilization pattern of *Streptomyces sp.* MA6858 at 21 days | |
|---|---|
| Carbon source | Utilization |
| D-arabinose | 0 |
| L-arabinose | 1 |
| cellobiose | 2 |
| D-fructose | 2 |
| inositol | 0 |
| α-D-lactose | 2 |
| β-D-lactose | 3 |
| D-maltose | 0 |
| D-mannitol | 1 |
| D-mannose | 3 |
| D-raffinose | 1 |
| L-rhamnose | 1 |
| sucrose | 0 |

| Carbohydrate utilization pattern of Streptomyces sp. MA6858 at 21 days | |
| --- | --- |
| Carbon source | Utilization |
| D-xylose | 0 |
| L-xylose | 0 |
| a-D-glucose (control) | 2 |

3 = good utilization
2 = moderate utilization
1 = poor utilization
0 = no utilization Comparisons of MA 6858 to the three Streptomyces strains known to produce FK-506/FK-520/FK-523 show very little similarity. The known producers of FK-520 and FK-523 are members of the *Streptomyces hygroscopicus* species complex. Both strains belong to the gray color series, both produce spores on spiral sporophores and both exhibit coalescence of the aerial spore mass during maturation. These characteristics clearly distinguish these strains from MA 6858. Comparison of MA 6858 with *Streptomyces tsukubaensis* also reveals considerable phenotypic differences. MA 6858 belongs to the white or yellow color series, while *S. tsukubaensis* belongs in the gray color series. Coloration of the vegetative mycelium also differs, with MA 6858 ranging from orange yellow to medium yellow brown and *S. tsukubaensis* ranging from pale pink to reddish orange to pale brown. MA 6858 utilizes starch and produces $H_2S$ whereas *S. tsukubaensis* does not. Significant differences are also observed in the carbon source utilization patterns of these strains. MA 6858 utilizes D-fructose, lactose, rhamnose, raffinose, arabinose, and mannitol whereas *S. tsukubaensis* does not. *S. tsukubaensis* utilizes sucrose and maltose whereas MA 6858 does not.

The above-described results of DNA-DNA homology studies are indicative of a genus level relationship among these strains. However, MA 6858 is neither a strain of *Streptomyces hygroscopicus* nor a strain of *Streptomyces tsukabaensis* and is believed to be a unique strain on the basis above-described comparative analysis.

The present invention process can be practiced with any "FK-506-producing" strain of Streptomyces sp., family and particularly preferred is the (MA 6858) ATCC No. 55098 strain.

In general, FK-506 can be produced by culturing (fermenting) the FK-506 substance-producing strain in an aqueous nutrient medium containing sources of assimilable carbon and nitrogen, preferably under submerged aerobic conditions (e.g. shaking culture, submerged culture, etc.). The aqueous medium is preferably maintained at a pH of about 7-8 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distilled solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As the conditions for the production of FK-506 in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of FK-506. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the vegetative inoculum is produced, is substantially the same as or different from the medium utilized for the production of FK-506 and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 80 hours to 120 hours, which may be varied according to fermentation conditions and scales. Preferably, the production cultures are incubated for about 96 hours at 27° C. on a rotary shaker operating at 220 rpm, wherein the pH of the fermentation medium is maintained at 7.0 to harvest.

Media for culturing/production and carrying out the fermentation include the following:

| BaSa Seed Medium | |
| --- | --- |
| Ingredient | Per Liter |
| $KNO_3$ | 2 gm |
| Glucose | 20 gm |
| Yeast Extract (Fidco) | 20 gm |

-continued

| | |
|---|---|
| HyCase SF (Sheffield) | 20 gm |
| NaCl (12.5% Stock) | 4 mL |
| MgSO$_4$.7H$_2$O (12.5% Stock) | 4 mL |
| MnSO$_4$.H$_2$O (0.5% Stock) | 1 mL |
| ZnSO$_4$.7H$_2$O (1.0% Stock) | 1 mL |
| CaCl$_2$.2H$_2$O (2.0% Stock) | 1 mL |
| FeSO$_4$.7H$_2$O | 25 mgm |
| Adjust to pH 7.0 with 5 N NaOH | |
| Distilled H$_2$O q.s. | 1 Liter |
| add 25 mL/250 mL Baffled Erlenmeyer flask, cotton closure | |
| Autoclave 20', 121° C. | |

KE Seed Medium (Soil Actinomycetes)

| Component | g/L |
|---|---|
| Dextrose | 1.0 |
| Dextrin | 10.0 |
| Difco beef extract | 3.0 |
| Ardamine pH | 5.0 |
| NZ Amine E | 5.0 |
| MgSO$_4$.7H$_2$O | 0.05 |
| Phosphate Buffer pH 7.0 | 2.0 ml |
| (a) KH$_2$PO$_4$-91.0 g in 1000 ml distilled H$_2$O | |
| (b) Na$_2$HPO$_4$-95.0 g in 1000 ml distilled H$_2$O | |
| Mix 11 ml (a) and 19 ml (b) for pH 7.0 buffered solution. | |
| CaCO$_3$ | 0.5 g |
| Distilled H$_2$O | 1000 ml |
| Adjust to pH 7.0-7.2 with NaOH. Then add CaCO$_3$ before sterilization | |

KJ-2 Production Medium

| Component | g/L |
|---|---|
| Glucose | 25.0 |
| Corn Steep Liquor | 15.0 |
| Distillers Solubles | 10.0 |
| Pharmamedia | 5.0 |
| CoCl$_2$.6H$_2$O | 10 mg |
| Distilled H$_2$O | 1000 ml |
| CaCO$_3$ | 3.0 |
| Adjust to pH 7.3 before sterilization | |

FKA Production Medium

| Component | g/L |
|---|---|
| Soluble Starch | 45.0 |
| Corn Steep Liquor | 10.0 |
| Dried Yeast | 10.0 |
| Distilled H$_2$O | 1000 ml |
| CaCO$_3$ | 1.0 |
| P-2000 | 1 ml |
| Adjust to pH = 6.8 prior to sterilization | |

Sterilization conducted by: autoclaving 50 ml medium/250 ml Erlenmeyer flask (non-baffled), for 20 minutes at 121° C., 15 psi.

The produced FK-506 can be recovered from the culture medium by conventional means, e.g. high pressure liquid chromatography (HPLC), which are commonly used for the recovery from broths of other known biologically active substances. The FK-506 substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation excchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The broth from the fermentation exhibits positive immunosuppressive activity by the "T-cell proliferation assay" and possesses utility on this basis.

The product FK-506 exhibits the following physical characteristics:
1. White amorphous powder
2. Solubility in methanol
3. Molecular ion (m/z 803) and fragment ions, as determined by electron ionization mass spectroscopy, consistent with FK-506
4. Proton nuclear magnetic resonance spectrum consistent with FK-506.

The FK-506 obtained according to the fermentation processes as explained above can be isolated and purified in a conventional manner, for example, extraction, precipitation, fractional crystallization, recrystallization, chromatography, and the like.

The FK-506 of the present invention possesses pharmacological activity such as immunosuppressive activity, as described in U.S. Pat. No. 4,894,366, and therefore, useful for the treatment and prevention of the transplantation rejection of organs or tissues such as heart, kidney, liver, medulla ossium, skin, etc., graft-versus-host diseases by medulla ossium transplantation and the like.

The following examples are given for the purpose of illustrating the present invention and should not be construed as being limitations on the scope or spirit of the instant invention.

EXAMPLE 1

MA 6858 Culture Isolation

A sample of a fermentation broth was streaked for isolation onto AK agar medium and then incubated at 28° C. The agar composition is as follows:

| AK Agar Medium | |
|---|---|
| Agar | 20.0 g |
| Dextrose | 10.0 g |
| Asparagine | 1.0 g |
| K$_2$HPO$_4$ | 0.1 g |
| MgSO$_4$.7H$_2$O | 0.5 g |
| Yeast Extract | 0.5 g |
| Trace Elements | 10 ml* |
| Distilled H$_2$O | 1000 ml |
| pH 7.2 | |
| *FeSO$_4$.7H$_2$O | 1000 mg |
| MnSO$_4$.4H$_2$O | 1000 mg |
| CuCl$_2$.2H$_2$O | 25 mg |
| CaCl$_2$ | 100 mg |
| H$_3$BO$_3$ | 56 mg |
| (NH$_4$)$_6$Mo$_7$O$_{24}$.4H$_2$O | 19 mg |
| ZnSO$_4$.7H$_2$O | 200 mg |
| 0.1N HCl | 1000 ml |

The broth showed positive immunosuppressive activity as a regulator of T-cell proliferation activity by the procedure described as follows:

"Interleukin-2 Release Inhibition Assay"

"The FS. 6 T hybridoma cell line produces IL-2 when stimulated with concanavalin A (Con A). Compounds to be tested were first dissolved in DMSO (2 mg/mL) and then diluted to appropriate concentrations with RPMI 1640. FS.6 cells ($4 \times 10^3$ in 0.2 mL complete medium) stimulated with 6.7 µg/mL Con A were cultured in each well of the flat-bottomed 96-well microtiter plate with or without compounds. Complete medium consisted of RPMI 1640 supplemented with 10% fetal calf serum, 2 mM L-glutamine, 0.1 mM nonessential amino acids, $2 \times 10^{-5}$M 2-mercaptoethanol, 100 U/mL penicillin, and 100

μg/mL streptomycin. After 24 hours incubation (37° C., 5% $CO_2$), the supernatant of each culture was collected and IL-2 activity assessed by the ability of the supernatants to support proliferation of an IL 2-dependent T cell line CTLL. $4 \times 10^3$ CTLL cells in 0.1 mL complete medium was cultured with 0.1 mL of test supernatant (diluted 1:8 with complete medium). After 20 hours of incubation at 37° C., the cultures were incubated for four hours with MTT, [3-(4, 5-dimethylthiazol-2-yl)-2, 5-2H-diphenyltetrazolium bromide, at 0.45 mg per mL. The optical density (O.D.) of the culture was then measured with a 96 well Titertek ® multiscan reader at 570 nm. The effect of each compound on IL-2 production was expressed as percent inhibition, which was calculated as follows:

Percent Inhibition =

$$\left( O.D. \text{ of control culture} - \frac{O.D. \text{ culture containing test compound}}{O.D. \text{ control culture}} \right) \times 100.$$

After 7-10 days incubation, a morphologically distinct colony-type was observed to have grown on the agar medium. Microscopic observation of this colony-type showed it to be a Streptomyces. The Streptomyces was isolated into pure culture, fermented to produce a broth, which was then tested for T-cell proliferation activity as described in Example 2. It was found to be bio-active. The active pure culture was deposited in the Merck Culture Collection with accession number MA 6858.

Fermentation

A seed culture was produced by inoculating 50 ml of BaSa Seed Medium or KE seed medium (described above) in a 250 ml triple baffled erlenmeyer flask with 2-4 ml of a slant suspension of MA 6858. The culture vessel was incubated at 27° C. and shaken at 220 rpm under 85% humidity. After 48 hours incubation, the seed culture was sufficiently grown to be used as an inoculum.

The production media KJ-2 and FKA, described previously, (44 ml per 250 ml unbaffled erlenmeyer flask) were inoculated with 2 ml of seed culture and incubated under the temperature, shaker flask and humidity conditions described previously for 4-7 days. At daily intervals during incubation, a sample (2 ml) was aseptically removed from the production culture and tested for T-cell proliferation activity, i.e. immunosuppressive (IP) activity. Whole flasks were harvested following 4 or 7 days fermentation. The standard conditions (KE seed for 48 hours, KJ-2 production for 4 days) yielded IL-2 activity which was identified as FK-506 (approximately 10 μg/ml). In this experiment, the highest 4 day titer was obtained from 42 hour BaSa seed transferred into FKA production medium, yielding 33.3 μg/ml FK-506. The highest 7 day titer was 37.8 μg/ml FK-506 from FKA medium inoculated with 72 hour KE seed; 72 hour BaSa seed in the same medium (FKA) yielded 35 μg/ml FK-506.

Isolation and Purification Procedure of the Broth

To a 40 mL batch of whole fermentation broth described above was added 30 mL of MeOH and the mixture was stirred for 1 hour. The sample was filtered through a pad of Super-cel in a sintered glass funnel. The filtrate was passed through two Waters C-18 Sep-Pak cartridges hooked in series which had been preconditioned with 10 mL of MeOH followed by 20 mL of water. The Sep-Paks were washed with $2 \times 5$ mL of 50% aqueous MeOH then eluted with 5 mL of 100% MeOH. The MeOH eluate was dried in vacuo and then redissolved in 250 μL of MeOH. The concentrated eluate was purified by reverse phase HPLC using a Whatman ODS-3 column $0.94 \times 25$ cm. The 250 μL sample was injected onto the column which was equilibrated and eluted with 50:50, AcCN: 0.2% aqueous triflouroacetic acid flowing at 5 mL/min. The fractions eluting at 18-20 min were pooled and dried down to give the sample. Bioassay by the IL-2 assay (Example 2) indicated that this was the active material. The sample was submitted for mass spectral analysis and a proton NMR was obtained. The analytical results demonstrated that the compound isloated was identical to Fujisawa's FR-900506 (FK-506) as described in EPO Publication NO. 0184162 and U.S. Pat. No. 4,894,366.

EXAMPLE 2

T-Cell Proliferation Assay

1. Sample Preparation

An equal volume of methanol was individually added to a 1 ml sample to several of the above broths producing a 1:2 whole broth equivalent (WBE). The samples were centrifuged at 3,000 rpm for 5 minutes and the resulting supernatants were used as starting materials for the T-cell proliferation assay.

2. Assay

Spleens from C57B1/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $10^6$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 100 μl/well. The control, being the medium without test drug, and various below-indicated dilutions of the sample (above-described extracts) to be tested were then added in triplicate wells at 10 μl/well. FK-506 was used as a standard. The culture plates were then incubated at 37° C. in a humidified atmosphere of 5% $CO_2$-95% air for 44 hours. The proliferation of T lymphocytes was assessed by the colorimetric MTT method as described above (Example 1) and calculated as follows:

$$\% \text{ Inhibition} = \left(100 - \frac{\text{Mean } O.D. \text{ sample tested}}{\text{Mean } O.D. \text{ control medium}}\right) \times 100.$$

The results of % inhibition at various dilutions of the transformation medium FKA showed the sample to have substantially the same bioactivity profile as FK-506. Further, inhibition of T-cell proliferation by the sample was reversed by the addition of 100 units/ml of IL-2 (recombinant IL-2) at the initiation of culture.

Results are given in the following table:

| Inhibition of T Cell Proliferation by MA 6858 Culture Broth | | |
|---|---|---|
| | % Inhibition | |
| Dilution | No IL-2 | +IL-2 |
| 1/25,000 | 93 | 12 |
| 1/50,000 | 83 | 10 |
| 1/100,000 | 37 | 5 |
| 1/200,000 | 9 | 3 |

Notes to the Table:
1. Mouse T cell cultures were pulsed with MTT for 4 hours prior to harvesting at 48 hours.
2. Standard FK-506 (1ng/ml) gave 100% inhibition.
3. The inhibition of T cell proliferation was reversed by the addition of 50 Units/ml (+IL-2) of human recombinant IL-2 at the initiation of the cultures.

What is claimed is:

1. A biologically pure culture of the microorganism, Streptomyces sp., ATCC No. 55098.

* * * * *